US00PP30759P3

(12) United States Plant Patent
Maillard et al.

(10) Patent No.: US PP30,759 P3
(45) Date of Patent: Jul. 30, 2019

(54) PEACH TREE NAMED 'FLATCANDY'

(50) Latin Name: ***Prunus persica* (L.) Batsch**
Varietal Denomination: FLATCANDY

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/732,470

(22) Filed: Nov. 17, 2017

(65) Prior Publication Data

US 2018/0153071 P1 May 31, 2018

(30) Foreign Application Priority Data

Nov. 25, 2016 (QZ) ..... PBR 2016/2956

(51) Int. Cl.
*A01H 5/08* (2018.01)
*A01H 6/74* (2018.01)

(52) U.S. Cl.
USPC ..... Plt./195
CPC ..... *A01H 6/7463* (2018.05); *A01H 5/08* (2013.01)

(58) Field of Classification Search
USPC ..... Plt./156, 180, 194, 195
See application file for complete search history.

*Primary Examiner* — Susan McCormick Ewoldt
*Assistant Examiner* — Karen M Redden
(74) *Attorney, Agent, or Firm* — Westerman, Hattori, Daniels & Adrian, LLP

(57) ABSTRACT

A new and distinct variety of white flat peach tree denominated 'FLATCANDY' having an early season of maturity and which have fruits with high eating quality and very long shelf life without alteration before and after harvesting, with a semi-sweet white flesh with a red pigmentation, and a red pigmentation around the stone cavity, and an attractive skin with a very high percentage of purple red blush on skin surface, sometimes covering the whole surface or on a red background.

4 Drawing Sheets

Botanical classification: *Prunus persica* (L.) Batsch.

Variety denomination: 'FLATCANDY'.

This application claims priority of Community plant variety right No. 2016/2956 filed on Nov. 25, 2016 (Nov. 25, 2016) which is hereby incorporated by reference in its entirety.

BACKGROUND OF THE NEW VARIETY

The present invention relates to a new and distinct variety of white flat peach tree, *Prunus persica* (L.) Batsch, which has been given the variety denomination 'FLATCANDY'. The new variety named 'FLATCANDY' is also known as 4N.14E.161.13PBPL or ASF1491. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'FLATCANDY', the provisional reference of this peach tree variety was 4N.14E.161.13, corresponding to the tree 161 located in line 14E of the parcel 4N and selected during the year 2013. The letters "PBPL" are related to the first letters of the type of tree in French (PBPL for "Pêche Blanche PLate", that means "white flat peach"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'FLATCANDY', the clone reference was 'ASF1491'.

This new tree produces fruits with a long shelf life without alteration both on the tree after growth completion and after harvesting, very good eating quality, semi-clingstone white flesh fruits with a red pigmentation and in a star shape around the stone cavity, for fresh market in June in the Pyrénées-Orientales department, France.

ORIGIN OF THE VARIETY

The 'FLATCANDY' white flat peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'FLATCANDY' variety results from a controlled cross between the white nectarine variety named 'ASF0621' (not patented) which was used as the seed parent, and the white flat peach variety named 'FLATREINE' also known as ASFPBF0796 (U.S. Plant Pat. No. 22,495) which was used as the pollen parent.

The 'FLATCANDY' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'FLATCANDY' white flat peach tree blooms at the end of February or early in March near Elne in the Pyrénées-Orientales department, France. The blooming period is considered medium. However, it was observed that its date of blooming seems to be highly dependant on climatic conditions.

The first fruit of 'FLATCANDY' ripens generally early season, during June. More particularly, ripening time usually begins from June 16$^{th}$, until June 28$^{th}$. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
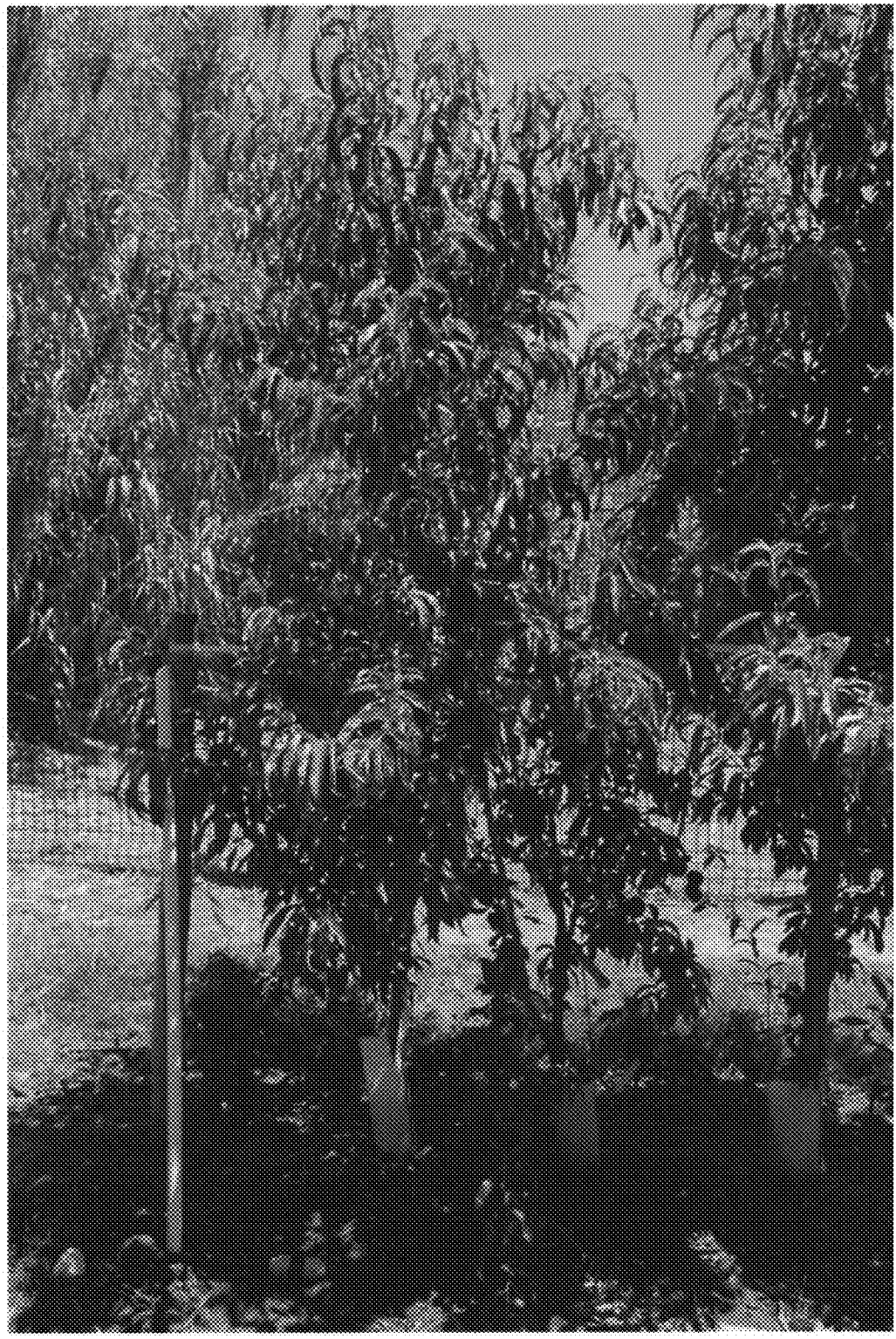
FIG. 1 is a color photograph showing a tree of the new variety in orchard.
Figure 2:
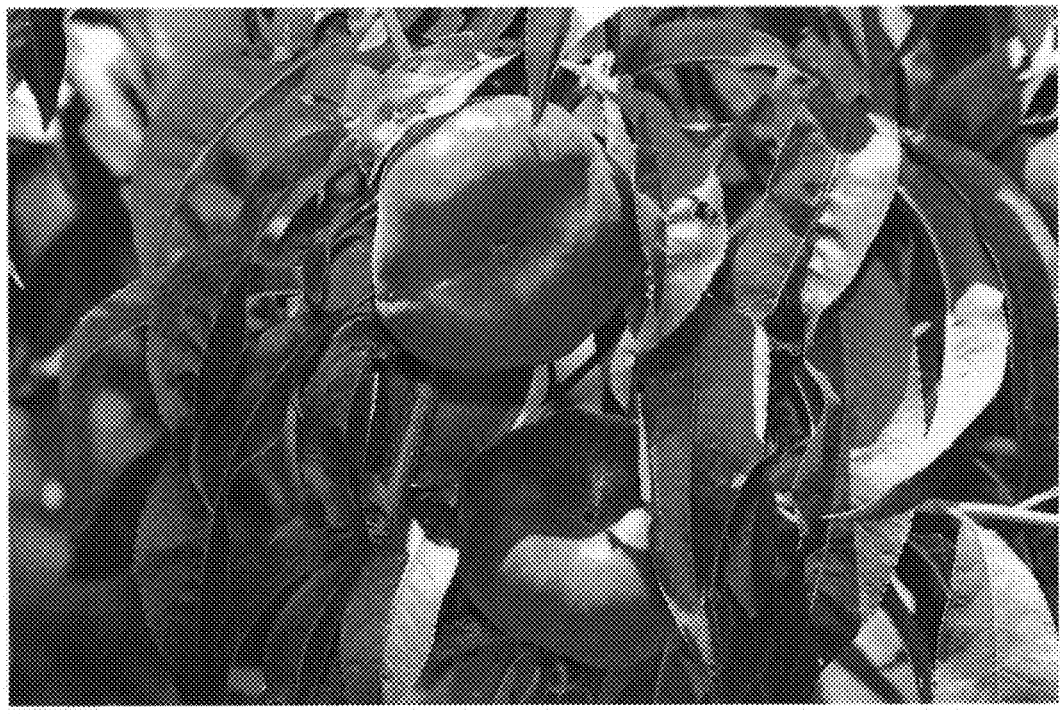
FIG. 2 is a color photograph that shows a close view of typical specimens of the fruit of the new variety 'FLATCANDY' on a branch of the tree.
Figure 3:
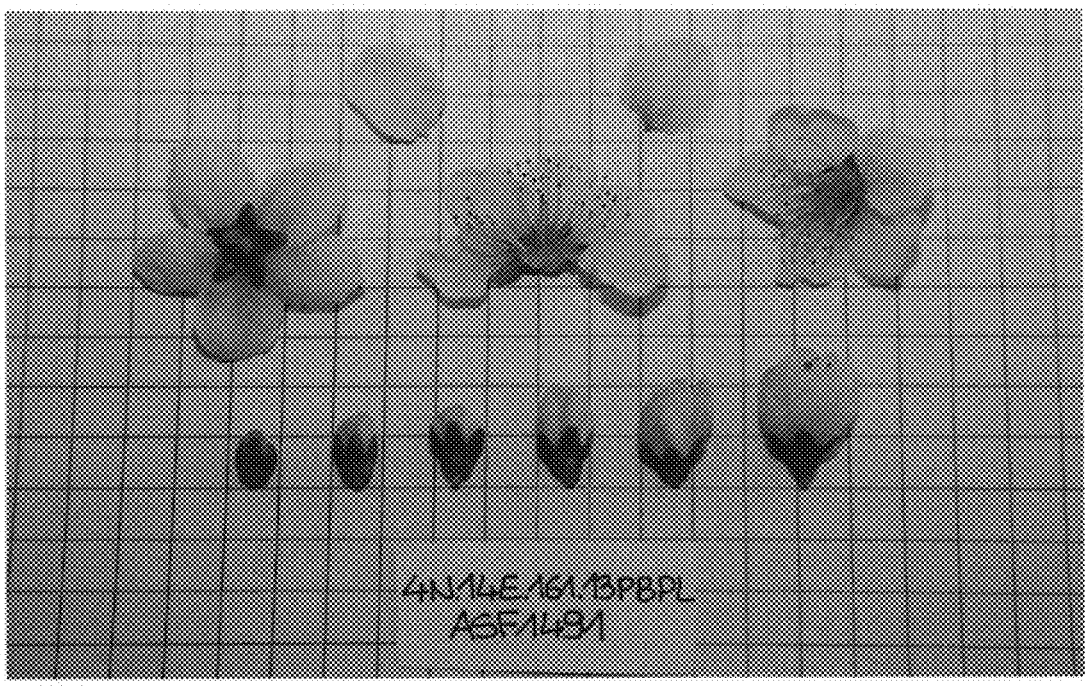
FIG. 3 is a color photograph which depicts the flower buds at different development stages, and the reverse and side view of the flower and the reproductive organs with petals removed, of the new variety.
Figure 4:
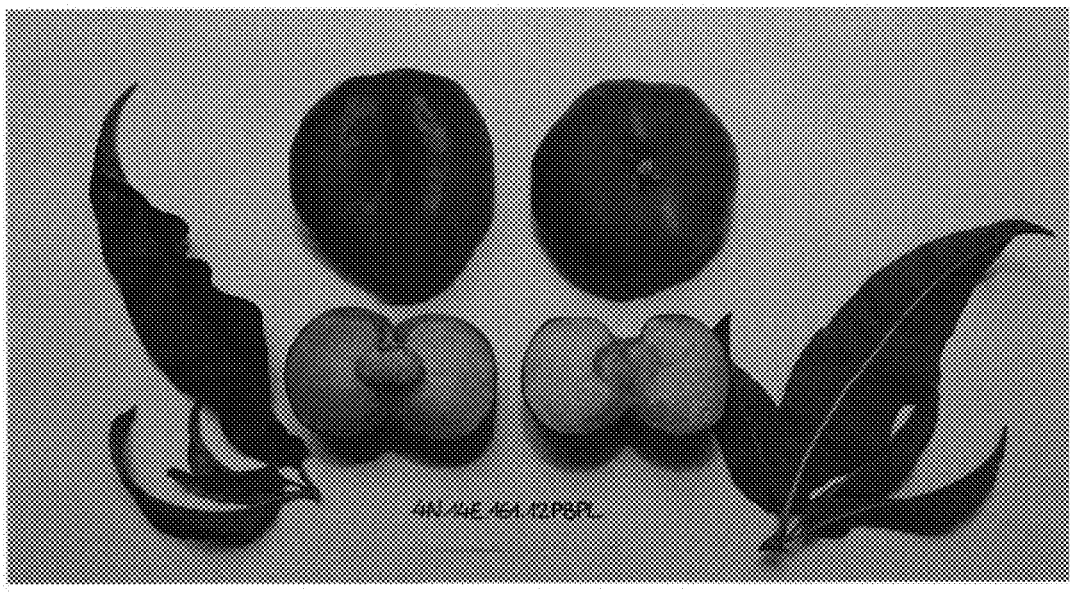
FIG. 4 a close view of three typical specimens of the fruit of the new variety 'FLATCANDY' at ripening time, one fruit having been cut in half with the pit being left in one of the halves for depicting leaves, fruit flesh, pit and pit cavity of the new variety.
Figure 5:
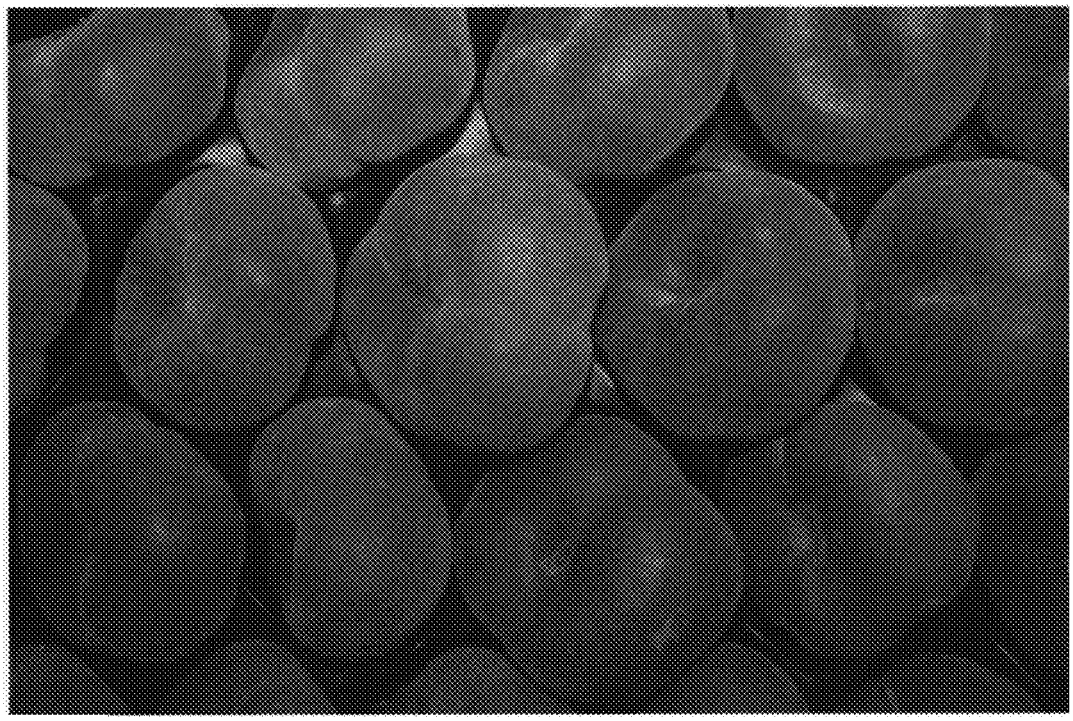
FIG. 5 is a color photograph that shows a close view of typical fruits after harvesting.
Figure 6:
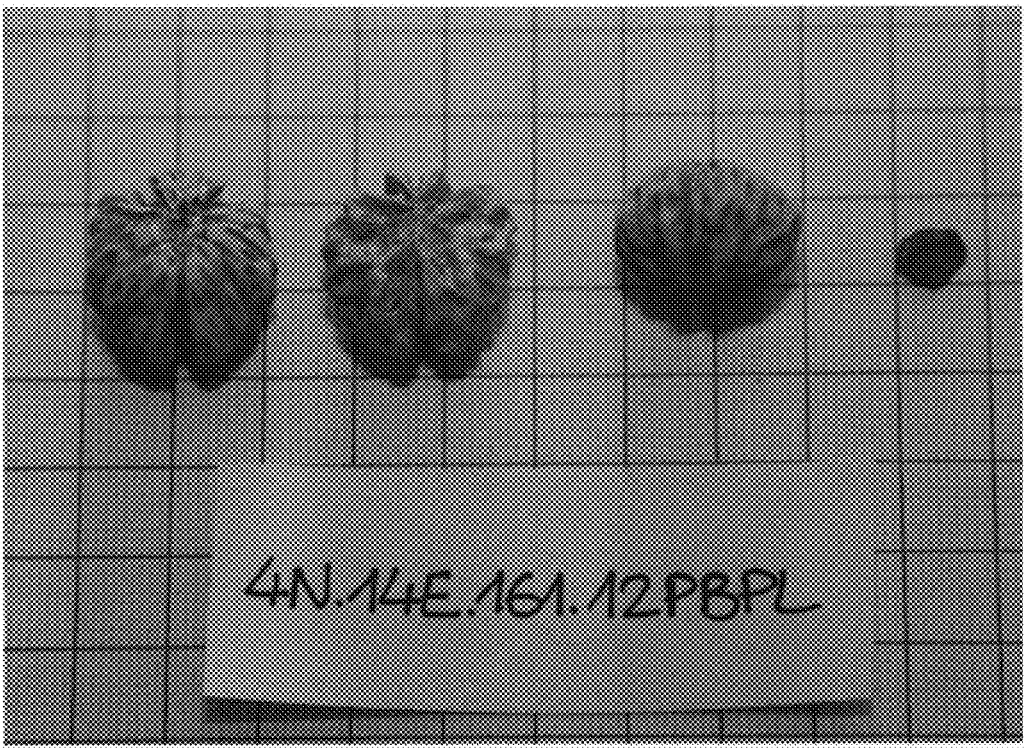
FIG. 6 is a color photograph that shows different views of the stone of the new variety, and a view of the kernel removed from the stone.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'FLATCANDY' is high, due to fruit very long shelf life without alteration after harvesting.

Trees are vigorous and large stature half-standing in a semi-flared out aspect. The anthocyanic coloration of flowering shoot is present excluding brushwood side away from sun. The time of beginning of flowering is considered medium; flowering begins at the end of February or during March. The type of flower is showy (rosette) with large petal size. Petals are pale to medium pink. Leaf glands are present and reniform. The fruit flesh is white with a red pigmentation, also around the stone cavity in a star shape. The fruit skin is thick, with a purple red blush on a red background. The stone is semi-clingstone and its size is small. Fruit taste is semi-sweet, very aromatic and with a high level of sugars.

Compared to 'FLATBELLA' white flat peach variety (U.S. Plant Pat. No. 23,194), the fruits of 'FLATCANDY' variety generally ripen one week earlier, and sometime even more than one week earlier. The fruits skin color of 'FLATCANDY' variety is more intense and purple red compared to skin color of 'FLATBELLA' variety, which is considered pink red.

Compared to 'FLATWO' (U.S. Plant Pat. No. 29,635) variety, the fruits of the new variety 'FLATCANDY' generally ripen two weeks later.

Compared to its seed parent, the selection 'ASF0621', 'FLATCANDY' variety is a flat peach whereas 'ASF0621' is a round nectarine. Whereas fruit taste of 'ASF0621' is balanced to acid, 'FLATCANDY' is a semi-sweet variety.

Compared to its pollen parent 'FLATREINE' also known as ASFPBF0796 (U.S. Plant Pat. No. 22,495), the fruits of 'FLATCANDY' variety generally ripen almost 1 month earlier.

DETAILED DESCRIPTION

Referring more specifically to the pomological details of this new and distinct variety of white flat peach tree, the following was observed on trees in their fourth growing season (third year of production) under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered medium.

*Productivity.*—Considered good to very good, and regular. Fruit set is spaced by thinning to develop the remaining fruit into the desired market sized fruit.

The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting flat fruits, significantly promotes fruit qualities, especially growth, color and firmness. Moreover, contamination risks due to monilia or rot are significantly reduced. 'FLATCANDY' variety is not much sensitive to cracking of pistil cavity, to cork formation into peduncle cavity or to monilia. The productivity is approximately 25 metric tons per hectare.

*Bearer*.—Very regular. The fruit distribution is considered homogenous on mixed branches and spurs having more than 1 year. Thinning of 2 fruits out of 3 was necessary for the tree valorisation. Thinning was necessary every year during the years of observation.

*Form*.—The 'FLATCANDY' variety has naturally a semi-flared shape.

*Density*.—Considered dense.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. Traditionally, flat fruits are more sensitive to critical low temperatures and to climatic variations, because of the flower morphology in which the ovule is less protected than in the classical round fruits. Thus, areas not much exposed to frost are recommended for trees growth. However 'FLATCANDY' trees seem to be very resistant to critical frosty weather.

Trunk:

*Diameter*.—Approximately 39.0 to 45.0 millimeters in diameter when measured at a distance of approximately 20.0 centimeters above the soil level.

*Bark texture*.—Considered rough, with lenticels.

*Lenticels*.—Numerous lenticels are present. The number of lenticels reaches 5 lenticels per $cm^2$.The lenticels range in size of approximately 3.0 to 4.5 millimeters in width, and about 1.5 to 1.7 millimeters in height.

*Lenticel color*.—The lenticels show a beige to light orange color (RHS Greyed Orange 165 C or RHS Greyed Orange 165 D).

*Bark coloration*.—The bark has a brown to grey color (RHS Grey Brown N 199 B) slightly darker than the outside of lenticels color.

Branches:

*Size*.—The branches are pruned to approximately 1.0 meter in length.

*Diameter*.—Average as compared to other peach varieties. The current season shoots have a diameter of approximately 5.0 to 6.0 millimeters, and mature branches have a diameter of approximately 8.0 to 9.0 millimeters.

*Surface texture*.—Smooth for current season shoots. Rough, with lenticels, for mature branches. Wood which is several years old has no furrowed appearance.

*Crotch angles*.—Primary branches are considered variable, but the crotch angles are generally 75 degrees from the horizontal axis. This particular characteristic is not considered distinctive of the variety, however.

*Current season shoots*.—

*Internode length*.—Generally 20.0 to 25.0 millimeters.

*Color*.—The color of new shoot tips is considered green (RHS Yellow Green 144 A) on lower part of new shoot tips, whereas the upper part is darker and colored in brown-purple (RHS Greyed Purple 183 B), depending on the level on the tip and the sunlight exposure.

*Mature branches*.—

*Internode length*.—Generally 18.0 to 23.0 millimeters.

*Color of mature branches*.—Brown (RHS Grey Brown 199 A or RHS Grey Brown N 199 A or RHS Grey Brown N 199 B).

*Lenticels*.—Numerous lenticels are present on mature branches. The number of lenticels reaches 4 lenticels per $cm^2$. The size of lenticels is considered small. The lenticels range in size from approximately 1.8 to 2.0 millimeters in width, and about 0.9 to 1.2 millimeters in height. The lenticel shape is round and slightly stretched.

*Lenticel color*.—The lenticels on mature branches have a light beige color (RHS Greyed Yellow 162 D).

Leaves:

*Size*.—Considered medium for the species. The ratio leaf length/leaf width is 4.04.

*Leaf length*.—Approximately 145.0 to 163.0 millimeters without leaf petiole. The medium length is about 152.6 millimeters.

*Leaf width*.—Approximately 33.0 to 42.0 millimeters. The medium width is 37.8 millimeters.

*Leaf base shape*.—Concave.

*Leaf form*.—Lanceolate.

*Leaf tip form*.—Acuminate.

*Leaf color*.—

*Upper leaf surface*.—Yellow Green (RHS Yellow Green 147 A).

*Lower surface*.—A lighter green (RHS Yellow Green 146 A) than the upper leaf surface color.

*Leaf texture*.—Smooth and glabrous on both upper and lower surfaces of the leaf.

*Leaf venation*.—Pinnately veined.

*Mid-vein*.—

*Color*.—Light green, almost cream white (RHS Yellow Green 145 D). The color may evolve with maturity.

*Leaf margins*.—Slightly undulating.

*Form*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Length*.—About 10.0 to about 13.0 millimeters.

*Diameter*.—About 1.5 to 2.0 millimeters.

*Petioles color*.—

*Upper petiole surface*.—Light green (RHS Yellow Green 144 A).

*Lower surface*.—Light green (RHS Yellow Green 144 C).

*Leaf glands.*—

*Size.*—Considered medium to large. Their length is about 2.0 millimeters and their width is about 1.0 millimeter.

*Number.*—Generally 2 glands per leaf.

*Type.*—Reniform.

*Margins.*—Smooth and regular.

*Color.*—On young leaves, leaf glands color is considered a light green (RHS Green 145 B). On older leaves, leaf glands color turns to a dark brown (RHS Grey Brown 199 A to RHS Grey Brown 199 B).

*Leaf stipules.*—

*Generally.*—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are conic in form with a round tip. Their form is evolving until blooming, with variable dimensions. Just before blooming, floral buds are between 9.0 and 11.0 millimeters wide and between 17.0 and 20.0 millimeters long.

*Color.*—This characteristic is dependent upon the proximity to bloom. At pre-floral stage of development, the bottom of the flowers buds, formed by the sepals, is of purple-brown color (RHS Greyed Purple 183 A or RHS Greyed Purple 183 B) on their outer surface and yellow green (RHS Yellow Green 144 A) on their inner surface. The corolla, formed by the petals, is generally of medium pink color (RHS Red Purple 65 B or RHS Red Purple 65 C) on both faces of the petals. Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins at the end of February or in March. The first bloom was observed on Mar. 11, 2015.

*Blooming time.*—Considered medium in relative comparison to other commercial peach cultivars grown in the Pyrénées-Orientales departement, France. The date of full bloom is observed generally at the middle of the blooming period. The date of bloom varies slightly with climatic conditions and cultural practices. Thus the full bloom was observed in 2015, from March 11$^{th}$ until March 19$^{th}$, then from February 26$^{th}$ until Mar. 4, 2016 and then from March 3$^{rd}$ until Mar. 11, 2017.

*Duration of bloom.*—Medium. Approximately between 8 to 9 days. This characteristic varies slightly with the prevailing climatic conditions.

*Flower type.*—The variety is considered to have a showy type flower.

*Flower size.*—Considered large. Flower diameter at full bloom is approximately 40.0 to 44.0 millimeters.

*Bloom quantity.*—Considered abundant, approximately between 35 and 50 flowers per meter, with a high rate of fruit set.

*Flower bud frequency.*—Generally 2 flower buds appear per node, occasionally 1.

*Petal size.*—

*Generally.*—Considered large.

*Length.*—Generally between 21.0 and 23.0 millimeters.

*Width.*—Generally between 19.0 and 21.0 millimeters.

*Petal form.*—Round-shaped.

*Petal count.*—Generally 5, sometimes more than 5.

*Petal texture.*—Smooth and glabrous on both upper and lower surfaces of the petal.

*Petal color.*—At the stage F of blooming, when the flower is fully opened, both surfaces of the petal are colored with a pale pink (RHS Red Purple 62 C) or a medium pink (RHS Red purple 65 B or RHS Red purple 65 C or RHS Red purple 65 D) when young, becoming slightly darker until the end of blooming.

*Fragrance.*—Sweet.

*Petal claw.*—

*Form.*—The claw is considered to have a narrow form.

*Length.*—About 1.5 to 2.0 millimeters.

*Width.*—About 1.5 to 2.0 millimeters at the base.

*Color.*—The petal claw usually shows a violet pink color darker than the petal color (RHS Red Purple 61 A or RHS Red Purple 61 B).

*Petal margins.*—Generally considered wavy, sinuate, near the base.

*Petal apex.*—

*Generally.*—The petal apices are generally round shaped as a wide dome.

*Flower pedicel.*—

*Length.*—Considered medium and having an average length of approximately 2.5 to 3.0 millimeters.

*Diameter.*—Considered average, approximately 1.0 to 2.0 millimeters.

*Color.*—Light green (RHS Yellow Green 144 A or RHS Yellow Green 144 B or RHS Yellow Green 145 A).

*Calyx.*—

*Internal surface texture.*—Smooth and glabrous.

*Color.*—At the stage F of blooming, when the flower is opened, the inner surface of the calyx, namely the flower receptacle, is greenish yellow (RHS Yellow Green 153 C or RHS Yellow Green 153 D). The outer surface of the calyx is considered of purple-brown color (RHS Greyed Purple 183 A or RHS Greyed Purple 183 B or RHS Greyed Purple 187 A) and yellow green near the base of the calyx (RHS Yellow green 144 A or RHS Yellow green 144 B).

*Sepals.*—

*Sepal count.*—Generally 5, sometimes 6.

*Surface texture.*—The outer surface has a short, fine pubescent texture. The inner surface has a smooth texture.

*Margins.*—Smooth.

*Size.*—Medium.

*Length.*—Approximately 5.0 to 6.0 millimeters.

*Width.*—Approximately 4.0 to 5.0 millimeters.

*Form.*—Conic and round at the top.

*Color.*—At pre-floral stage of development (stage A) the sepals are colored in purple-brown color (RHS Greyed Purple 183 A or RHS Greyed Purple 183 B) on their outer surface and yellow green (RHS Yellow Green 144 A) on their inner surface. At the stage F of blooming, the inner surface of the sepals is considered greenish yellow (RHS Yellow Green 146 A to RHS Yellow Green 146 B) and the outer surface of the sepals is considered of purple-brown color (RHS Greyed Purple 183 A or RHS Greyed Purple 183 B or RHS Greyed Purple 187 A) and yellow green near the base of the sepals (RHS Yellow green 144 A or RHS Yellow green 144 B).

*Anthers.*—

*Generally.*—Small to medium in length, approximately 0.5 millimeter.

*Color.*—At an early stage of maturity, anthers are colored with an orange yellow (RHS Yellow Orange 16 A to RHS Yellow Orange 16 B) or an orange red color (RHS Red Group N34 A or RHS Greyed Red Group 178 A) or red (RHS Orange Red N34 A).

*Shape.*—Cordate.

*Pollen production.*—Pollen is abundant, and has a yellow (RHS Yellow 12 A) or an orange yellow color (approximately RHS Yellow Orange 17 B to RHS Yellow Orange 17 C) which may evolve with maturity. The present variety is considered auto-fertile (self-pollinating).

*Filaments.*—

*Size.*—Medium length, between 12.0 and 18.0 millimeters in length. Filaments length is generally higher than the pistil's length.

*Color.*—Considered white (RHS White 155 D) or pale pink (RHS Red Purple 62 C or RHS Red Purple 62 D) to a slightly darker pink (RHS Red Purple 73 A or RHS Red Purple 73 B). The color becomes darker at the end of blooming (RHS Red Purple 65 A).

*Average number of stamens per flower.*—Generally between 35 and 44.

*Pistil.*—

*Number.*—Usually 1.

*Generally.*—Average in size.

*Length.*—Approximately 13.0 to 16.0 millimeters including the ovary. Generally smaller than or equal to filaments in length.

*Color.*—Considered a very pale green (RHS Yellow Green Group 151 D or RHS Yellow Green 150 D). The color evolves during the blooming to become more and more pale green (RHS Yellow Green Group 150 D) and sometimes very slightly pink (RHS Red Group 36 D) at the end of blooming.

*Ovary.*—

*Pubescence.*—Present.

*Height.*—Between 2.5 and 3.0 millimeters.

*Diameter.*—Between 1.5 and 2.0 millimeters.

*Color.*—Green (RHS Yellow Green 145 A or RHS Yellow Green 145 B).

*Stamen.*—Size compared to petals.—The size of stamen is smaller than the size of petals.

*Stigma.*—

*Position compared to anthers.*—The stigma is below the anthers.

*Diameter.*—Approximately 1.5 millimeters.

*Color.*—Yellow (RHS Yellow Green 151 B).

Fruit:

*Maturity when described.*—Very firm in ripe conditions (shipping ripe).

*Date of first picking.*—Jun. 16, 2014.

*Date of last picking.*—The date of harvest varies slightly with the prevailing climatic conditions. The 'FLATCANDY' variety has an early date of picking, and a grouped maturity. The maturity is grouped within 8 to 9 days and the harvest is generally performed in two runs. Last known picking times carry on June 16$^{th}$ to Jun. 23, 2014, then on June 20$^{th}$ to Jun. 28, 2015, then on June 28$^{th}$ to Jul. 5, 2016 and then on June 16$^{th}$ to Jun. 22, 2017.

*Size.*—

*Generally.*—Homogeneous in size. Considered medium.

*Average cheek diameter.*—Approximately 64.0 to 69.0 millimeters.

*Average axial diameter.*—Approximately 36.0 to 40.0 millimeters.

*Typical weight.*—Generally between 80.0 and 110.0 grams. This characteristic is high dependent upon the prevailing cultural practices, and therefore is not particularly distinctive of the variety.

*Fruit form.*—

*Generally.*—Round and flattened, generally with few bump. The fruit is generally uniform in symmetry, viewed from the suture's plane.

*Suture.*—

*Fruit suture.*—Wide-mouthed and slightly marked, extending from the base to the apex. No apparent callousing or stitching exists along the suture line. Not pointed.

*Color.*—The suture has generally a similar color to the whole fruit color, which is purple red (RHS Greyed Purple N186 C or RHS Greyed Purple 187 B).

*Ventral surface:*

*Form.*—Smooth.

*Apex.*—Slightly depressed.

*Base.*—Semi-flared, shallow.

*Stem cavity.*—Average depth of the stem cavity is about 6.0 to 8.0 millimeters. Average width is about 14.0 to 18.0 millimeters.

*Fruit skin.*—

*Thickness.*—Considered thick and strong, and the adherence of skin to flesh is strong to medium, depending on the fruit maturity.

*Texture.*—Very smooth for a peach variety.

*Taste.*—Semi-sweet, sugary.

*Tendency to crack.*—None observed.

*Color.*—

*Blush color.*—This blush color is purple red (RHS Greyed Purple N186 C or RHS Greyed Purple 187 B). The purple red blush covers 80 to 100% of the fruit skin surface on a red background (RHS Greyed Red 180 A or RHS Greyed Red 180 B) on approximately 0 to 20% of the fruit skin surface. The percentage of the blush on the fruit skin surface can vary, and is generally dependant upon the prevailing conditions under which the fruit was grown.

*Ground color.*—The ground color covers approximately 0 to 20% of the fruit skin surface, and is considered red (RHS Greyed Red 180 A or RHS Greyed Red 180 B).

*Fruit stem.*—Medium in length, approximately 7.0 to 8.0 millimeters.

*Diameter.*—Approximately 4.0 millimeters.

*Color*.—Pale green (RHS Yellow Green 145 A to RHS Yellow Green 145 B).

*Flesh*.—

*Ripens*.—Very homogenously, slowly. The flesh has a long shelf life.

*Texture*.—Very firm, very dense, crunchy, melting, juicy at harvest maturity stage.

*Fibers*.—Not fibrous.

*Aroma*.—Very pronounced.

*Eating quality*.—Considered very good, aromatic.

*Flavor*.—Considered semi-sweet. The Brix is generally superior to 9 and acidity comprised between 6 and 9 meq/100 ml.

*Juice*.—Juicy to very juicy at complete maturity.

*Brix*.—Generally 9.5 to 11.0 degrees. This characteristic varies slightly with the number of fruit per tree; prevailing cultural practices; and the surrounding climatic conditions.

*Flesh color*.—The flesh is considered white (RHS White 155 B) usually with a red pigmentation (RHS Red 47 A), also in a star shape around the stone cavity, on approximately 3.0 to 4.0 millimeters.

Stone:

*Type*.—Semi-Clingstone, more or less semi-adherent depending on the fruit maturity.

*Size*.—Considered small for the variety. The stone size varies significantly depending upon the tree vigor, crop load and prevailing growing conditions.

*Length*.—Approximately 22.0 millimeters.

*Width*.—Approximately 20.0 millimeters.

*Diameter*.—Approximately 15.0 millimeters.

*Form*.—Flattened.

*Base*.—Straight.

*Apex*.—

*Shape*.—The stone apex is flattened.

*Stone cavity*.—Considered small size, with flattened form and dimensions corresponding to the stone's dimensions.

*Stone surface*.—

*Surface texture*.—The pit is transversely furrowed on its entire surface. Furrows are deeper and more oblate on lateral sides.

*Ridges*.—The surface texture is generally characterized by more prominent ridges along the ventral edges and at the apical tip.

*Ventral edge*.—

*Width*.—Approximately 3.0 millimeters at mid-suture.

*Dorsal edge*.—

*Shape*.—Grooved.

*Stone color*.—The color of the dry stone is generally considered light orange brown (RHS Greyed Orange 165 C or RHS Greyed Orange 165 D).

*Tendency to split*.—Splitting is absent.

*Kernel*.—

*Size*.—The kernel is considered small.

*Length*.—Approximately 8.0 millimeters.

*Width*.—Approximately 7.0 millimeters.

*Thickness*.—Approximately 6.0 millimeters.

*Form*.—Considered flattened and elliptic. Sometimes double.

*Pellicle*.—The pellicle of the kernel has a short pubescence.

*Color*.—The kernel skin is orange-brown colored (RHS Greyed Orange N 167 B). The almond, which is the seed of the kernel, is white (RHS White 155 D) and has a bitter taste. The kernel and its embryo are mature at the time of fruit maturity.

*Use*.—The subject variety 'FLATCANDY' is considered to be a white flat peach tree having an early season of maturity, and which produces fruits that are considered firm, attractively colored in purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality*.—Considered very good. The fruit of the new white flat peach variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease*.—No particular susceptibilities were noted. The present variety is not very sensitive to Monilia or rot. The pistil cavity is completely closed, generally without any cork formation. More particularly, the leaves and branches are considered very few sensitive to powdery mildew (*Podosphaera leucotricha*), whereas the fruits are not sensitive to this disease. The new variety is moderately sensitive to blight (*Puccinia*), not sensitive to black bean aphid (*Aphis fabae*), moderately sensitive to leafhopper (belonging to Cicadellidae family). The fruits are slightly sensitive to monilia (belonging to Sclerotiniaceae family).

Although the new variety of white flat peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of white flat peach tree as illustrated and described, having an early season of maturity and characterized by fruits with high eating quality and very long shelf life without alteration before and after harvesting, with a semi-sweet white flesh with a red pigmentation, and a red pigmentation around the stone cavity, and an attractive skin with a very high percentage of purple red blush on skin surface, sometimes covering the whole surface or on a red background.

* * * * *